US006248372B1

(12) United States Patent
Mukerji et al.

(10) Patent No.: US 6,248,372 B1
(45) Date of Patent: Jun. 19, 2001

(54) BIOACTIVE RICE FLOUR EXTRACT USEFUL FOR TREATMENT OF HAEMOPHILUS INFLUENZAE INFECTIONS

(75) Inventors: Pradip Mukerji, Gahanna; Shie-Ming Hwang, Columbus; Yung-Sheng Huang, Upper Arlington; Jim-Wen Liu, Dublin, all of OH (US); Steven Neal Anderson, Aurora; Jonathan A. Meulbroek, Lake Forest, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/428,076

(22) Filed: Oct. 27, 1999

Related U.S. Application Data

(63) Continuation of application No. 09/035,603, filed on Mar. 5, 1998, now abandoned.

(51) Int. Cl.$^7$ .......................... A61K 35/78; A01N 65/00
(52) U.S. Cl. ................................................ 424/750
(58) Field of Search .......................................... 424/195.1

(56) References Cited

U.S. PATENT DOCUMENTS

| 5,489,440 | 2/1996 | Ndife et al. ........................... 424/489 |
| 5,498,408 | 3/1996 | Detra et al. ......................... 424/78.01 |

FOREIGN PATENT DOCUMENTS 0 345 710 A3   12/1989   (EP) .

OTHER PUBLICATIONS

Martha Windholz, Ssan Budavari, Edis., The Merek Index, 10th Ed., Merck Company, Inc., 6922 (1983).
Abstract of Japanese Patent 05139983 A, Jun. 08, 1993.

Brearley, C.A. and Hanke, D.E., "Pathways of synthesis of 3, 4–and 4, 5–phosphorlated phosphatidylinositols in the duckweed *Spirodela polyrhiza* L.," Biochem. J. (1993) 290, pp. 145–150.

Munnik, T., Irvine, R. and Musgrave, A., "Rapid turnover of phosphatidylinositol 3–phosphate in the green alga *Chlamydomonas eugametos*. signs of a phosphatidylinositide 3–kinase signaling pathway in lower plants?". Biochem. J. (1994) 298, pp. 269–273.

Brearley, C.A., and Hanke, D.E., "3–and 4–phosphorylated phosphatidylinositols in the aquatic plant *Spirodela polyrhiza* L.," Biochem. J. (1992) 283, pp. 255–260.

Yamamoto, K., Graziani, A., Carpenter, C., Cantley, L.C.., Lapetina, E.G., Medline Abstract, 1990, "A Novel Pathway for the Formation of Phosphatidylinositol 3, 4–bisphosphate. Phosphorylation of phosphatidylinositol 3–monophosphate by phosphatidylinositol–3–monophosphate 4–kinase," J. Biol. Chem., 1990, 265(36), pp. 22086–22089.

Carpenter, C.L., Duckworth, B.C., Auger, K.R., Cohen, B., Schaffhausen, B.S., Cantley, L.C., MedLine Abstract, 1990, "Purification and Characterization of Phosphoinositide 3–Kinase from Rat Liver," J. Biol. Chem., 1990, 265(32), pp. 19704–19711.

Food and Nutrition Bulletin, vol. 17, No. 2., Jun. 1996.

*Primary Examiner*—Sandra E. Saucier
*Assistant Examiner*—Vera Afremova
(74) *Attorney, Agent, or Firm*—Nickki L. Parlet; J. Michael Dixon

(57) ABSTRACT

The present invention is directed to a rice flour extract (RFE) which can be used in the prophylaxis and treatment of bacterial infections, particularly bacterial infections caused by *Haemophilus influenzae* and to a method of preparing and using such an antibacterial rice flour extract. The anti-*Haemophilus influenzae* rice flour extract of the present invention can be prepared from commercial food grade rice flours or non-commercial food grade rice flours.

22 Claims, No Drawings

BIOACTIVE RICE FLOUR EXTRACT USEFUL FOR TREATMENT OF HAEMOPHILUS INFLUENZAE INFECTIONS

This application is a continuation of application number 09/035,603, filed Mar. 5, 1998, now abandoned.

TECHNICAL FIELD

The present invention relates generally to a bioactive, antibacterial rice flour extract which can be used for prophylaxis and treatment of infections caused by *Haemophilus influenzae* and to a method of preparing and using such a bioactive rice flour extract.

BACKGROUND OF THE INVENTION

In the United States, otitis media, next to upper respiratory tract infections, is the most common cause for outpatient visits to pediatricians. Fifteen to twenty per cent of children younger than six years of age will contract otitis media. Otitis media is an inflammation of the middle ear characterized by symptoms such as otalgia, hearing loss and fever. One of the primary causes of these symptoms is a build up of fluid in the middle ear. Complications include permanent hearing loss, perforation of the tympanic membrane, acquired cholesteatoma, mastoiditis, and adhesive otitis. Children who develop otitis media in the first years of life are at risk for recurrent acute or chronic disease.

One of the primary causes of otitis media is *Haemophilus influenzae*, which is commonly known as "*H. influenzae*." It is thought that *H. influenzae* causes otitis media by adhering to nasopharyngeal cells. The adherence of *H. influenzae* to nasopharyngeal cells causes those cells to become infected and to produce secretions. The middle ear becomes infected because mechanical or functional obstruction of the Eustachian tube, which protects the middle ear from nasopharyngeal secretions, results in negative middle ear pressure. This negative pressure causes the nasopharyngeal secretions to enter the middle ear resulting in an infection, such as otitis media, usually with effusion.

Typically, otitis media is treated by means of administering a course of antibiotics consisting of a penicillin derivative. Other supportive therapies, such as analgesics, antipyretics and local heat are also helpful. Often, surgery is required to remove fluid from the middle ear and to relieve the pain experienced by the child.

Currently, no reliable prophylactic treatments are known. It has been demonstrated that human casein inhibits the adhesion of *H. influenzae* to human respiratory tract epithelial cells. See Aniansson et. al., *Microbial Pathogenesis* 1990;8:315–323. Aniansson, et al., found that human casein represents a new mechanism for the protection by breast-milk against respiratory tract infection. Thus, it is thought that human casein may be effective as a prophylactic treatment for otitis media but further study is required.

Rice flour is inexpensive, safe and easily obtained. Rice flour is made from rice kernels that have been either dehusked or dehusked and polished and then ground. Rice flour is a fine, powdery flour which is made from either brown rice or white rice which is ground to a particular size (coarse, regular, fine and extra fine). Brown rice is the entire rice grains with only the inedible outer husk removed. White rice is the rice grain which has had its husks, brans and germs removed. Typically, the majority of particles of coarse rice flour are smaller than 30 mesh; the majority of particles of regular rice flour are smaller than 50 mesh; the majority of particles of fine rice flour are smaller than 80 mesh; and the majority of particles of extra fine rice flour are smaller than 140 mesh.

Rice is also classified by grain lengths such as short-grain, medium-grain and long-grain. The length of long-grain rice is four to five time that of its width. When cooked, it produces light, dry grains that easily separate. Short-grain rice has fat, almost round grains that have a higher starch content than either the long-grain or the medium-grain varieties. When cooked, short-grain rice tends to be moist and viscous, causing the grains to stick together. Medium-grain rice has a size and character between the long-grain and the short-grain varieties. It is shorter and moister than long-grain rice and generally not as starchy as short-grain rice. Through fairly fluffy right after cooking, medium-grain rice begins to clump together upon cooling.

Rice flour has various types with different viscosities and gelatinization temperatures, depending upon the type of rice from which it is made and the process by which it is made. For example, exemplary rice flours include brown rice flours (long and medium-grain), white rice flours (long and medium-grain), waxy flours (short-grain), pregelatinized flours and mixed flours. Rice flour contains mostly carbohydrates (typically 79 to 81% by weight), some protein (typically 5% to 9% by weight), a small amount of fat (typically 0.5% to 1.3% by weight), moisture (typically 10% to 13% by weight), minerals (typically 0.2% to 0.8% by weight) and vitamins (typically about 16 ppm by weight).

Rice flour has been proposed as a basis for oral rehydration therapy, particularly for acute diarrheal diseases. See, e.g., U.S. Pat. No. 5,498,406 to Oltra, et al., entitled, "Oral Rehydration Composition." U.S. Pat. No. 5,489,440 to Ndife, et al., describes a method for making a rice flour-based oral rehydration solution. In this process, the rice flour is first gelatinized in water under heat and then cooled to permit enzymatic hydrolysis of the slurry of gelatinized rice flour. Next, protease and cellulase enzymes are added to the slurry to permit hydrolysis of the rice flour. The enzymes are then inactivated by heat and the slurry is cooled. A stabilizer, minerals and citric acid are added to the slurry and the slurry is homogenized. After homogenization, the solution is standardized by adding water and the product is sterilized. However, it should be noted that rice flour has not been previously proposed as a treatment for *H. influenzae* infections and their related complications.

For these reasons, a need still exists in the art for a composition and method for the prophylaxis and treatment of infections caused by *Haemophilus influenzae* and its clinical manifestations, such as, for example, otitis media.

DISCLOSURE OF THE INVENTION

The present invention is directed to a rice flour extract (RFE) which can be used in the prophylaxis and treatment of bacterial infections, particularly bacterial infections caused by *Haemophilus influenzae* and to a method of preparing and using such an antibacterial rice flour extract. The anti-*Haemophilus influenzae* rice flour extract of the present invention can be prepared from commercial food grade rice flours or non-commercial food grade rice flours. For example, food grade rice flour can be obtained in large quantities from several commercial sources. Useful suppliers include the following: Comet Rice Ingredients Company of Los Angeles, Calif.; Rivland Partnership of Houston, Tex.; and California Natural Products of Lathrop, Calif. A non-food grade rice flour can be obtained from ICN Biochemicals of Aurora, Ohio.

The rice flour extract of the present invention can be obtained in the following manner with commonly available reagents and materials. After selecting a rice flour, the rice flour is extracted under heat with an extraction solution having a neutral to alkaline pH until the rice flour solution becomes cloudy but does not completely gelatinize. For the purposes of this application, "gelatinization" occurs when one is not able to separate the liquid portion of the solution from the solid portion of the solution. A person of skill in the art is able to conduct viscosity measurements to determine the point at which complete gelatinization would be about to occur. Heat is used to break apart the starch granule but not to cause complete gelatinization of the rice flour. Useful aqueous extraction solutions include, but are not limited to, phosphate buffer solution (PBS) having a pH of about 7.20; a 0.1–0.2 N ammonium bicarbonate solution having a pH of from about 7.9 to about 8.0; or a 1% ammonium hydroxide solution having a pH of about 10.4.

Desirably, the rice flour solution is heated for at least about five minutes and, more desirably, it is heated for about five minutes to about two hours. The rice flour solution is heated at a temperature of about 30° C. to about 80° C. More desirably, the rice flour solution is heated at a temperature of about 37° C. to about 68° C. and, most desirably, it is heated at a temperature of about 50° C. to about 68° C. The extraction solution desirably has a pH of from about 4 to about 10.4. More desirably, the extraction solution has a pH of from about 7 to about 10 and, most desirably, the extraction solution has a pH of from about 7 to about 8.5.

The extract may then be diluted with additional extraction solution to facilitate the separation of insoluble residues and the filtration of extracts. Desirably, the diluted extract is centrifuged to separate a crude extract from insoluble residues. It is also desirable that the crude extract is sterile filtered.

The following examples are presented solely to illustrate the present invention. These examples are not intended, in any manner, to limit the invention as described or claimed.

The following example demonstrates the ability of rice flour extract to prevent the adhesion of *Haemophilus influenzae* to human nasopharynx cells.

EXAMPLE 1

ANTI-ADHESION ASSAY FOR *H. influenzae*

To determine the ability of rice flour extract to prevent the adhesion of *Haemophilus influenzae* to human nasopharynx cells, the following procedure was used. Detroit 562 human pharynx carcinoma cells (DT 562) were obtained from the American Culture Type Collection. A *Haemophilus influenzae* nontypeable bacterium strain, which was isolated from the middle ear of an infected child, was obtained from Dr. Lauren Bakaletz of Ohio State University.

The DT 562 cells were seeded into Costar 96 well plates at a density of 20,000 to 25,000 cells per well and were cultured in Dulbeco's modified Eagle Medium, available from Grand Island Biological Company. The cells were supplemented with 10% fetal bovine serum (FBS), available from Hyclone. The plates were incubated in a humidified atmosphere of 95% air and 5% carbon dioxide at 37° C. Plates containing cells were washed three times with 200 $\mu$L of Hanks Balanced Saline Solution (HBSS), available from Sigma Chemical Company of St. Louis, Mo., to remove serum proteins before the addition of bacteria in adhesion assays.

*Haemophilus influenzae* was streaked onto Chocolate agar plates, available from Becton Dickinson Diagnostic Instrument Systems of Sparks, Md., from frozen aliquots of a low passage number. The plates were then incubated at 37° C. in a humidified atmosphere of 95% air and 5% carbon dioxide for 18 hours to obtain logarithmically growing cultures. Bacteria harvested in phosphate buffered solution (PBS) supplemented with 0.05% bovine serum albumin (BSA), available from Miles Inc. of Kankakee, Ill., were centrifuged and resuspended in a volume of PBS/BSA yielding an optical density of 2.4 at a wavelength of 660 nm. 111-Indium-oxine ($^{111\text{-}}$In), a high-energy, short-lived tracer was ublized to radiolabel the bacteria. Fifty $\mu$Ci of $^{111\text{-}}$In solution was added to 2.5 mL of the bacterial suspension and incubated for 20 minutes at 37° C. The radiolabeled bacteria were then washed two times with 10 mL HBSS to remove unbound $^{111\text{-}}$In and resuspended in 5 mL HBSS supplemented with 30 mM N-2-hydroxyethylpiperazine-N'-2-ethane sulfonic acid buffer (HEPES), available from GIBCO. Twenty-five $\mu$L of the $^{111\text{-}}$In labeled bacterial suspension was preincubated with 25 $\mu$L of the rice flour extract in a polypropylene 96 well plate, available from Costar, for 15 minutes at 37° C. to allow binding of the test agent to the *Haemophilus influenzae* bacterium.

To determine the adhesion quantitation, the following procedure was used. Twenty-five $\mu$L of the preincubabon mixture containing radiolabeled bacteria and the rice flour extract was pipetted into each well of the assay plate containing DT 562 cells. The assay plate was incubated for about 15 to about 20 minutes at 37° C. to allow adhesion of the bacteria to the cell monolayer. Nonadherent bacteria were removed by washing the plate three times in HBSS. The assay was terminated by the addition of 100 $\mu$L of 0.05 N sodium hydroxide to disrupt the cell monolayer and the adhering of the *Haemophilus influenzae* bacterium. The contents of each well were then placed in Cobra polypropylene tubes and counted on a Cobra Gamma Counter, available from Packard Bell. After background radiation was subtracted from each well, the average count of four replicates (per sample) was calculated. Results are presented as the percent of inhibition of bacterial adhesion as compared to bacterial attachment in control wells containing no rice flour extract in which the percent of inhibition is zero.

Table 1 shows the percent extractable and percent inhibition of bacterial adhesion of various rice flour extracts.

TABLE 1

Bioactive PBS Crude Extracts of Rice Flours

| Rice Flour | Extracting Solvent | % Extractable | % Inhibition |
| --- | --- | --- | --- |
| ICN (lot 40838) | PBS | 1.7 ± 1.2(11) | 69 ± 8(11) |
| " | NH$_4$HCO$_3$ | 2 | 52 |
| Comet RF-M1080 | PBS | 2.7 ± 0.9(4) | 68 ± 10(4) |
| " | NH$_4$HCO$_3$ | 3.9 ± 0.2(5) | 71 ± 7(6) |
| Comet RF-W1120 | PBS | 16.9 | 63 |
| " | NH$_4$HCO$_3$ | 21.1 | 41 |
| Comet RF-L0080 | PBS | 2.3 | 46 |
| Rivland RM (lot 7577) | PBS | 5.8 | 73 |
| Rivland RL-100/JS-556 | PBS | 3.7 | 44 |
| Rivland RM-100/JS-556 | PBS | 4.7 | 57 |
| Rivland RL-100/JS-570 | PBS | 3.4 | 34 |
| Rivland RM-100/JS-570 | PBS | 5.4 | 49 |
| CNP WRF04224XFG | PBS | 18.6 | 58 |
| CNP WRF07084XFG | PBS | 21.1 | 63 |

*Values in parentheses are number of preparations or tests on separate days.

Table 2 shows the percent inhibition of bacterial adhesion of various ICN rice flour extracts (prepared from separate runs) at various test levels.

TABLE 2

ICN Rice Flour PBS Extracts Bioactivity

| Extract | Test Level (mg/mL) | % Inhibition |
|---|---|---|
| RFE-25 | 3.8 | 71 |
| RFE-54 | 0.8 | 70 |
| RFE-55 | 0.8 | 61 |
| RFE-1130-1 | 0.5 | 77 |
| RFE-58 | 0.5 | 73 |
| RFE-81 | 0.3 | 59 |
| RFE-85 | 0.3 | 48 |
| RFE-88 | 0.1 | 59 |
| RFE-89 | 0.2 | 59 |
| RFE-100 | 0.2 | 65 |

The extracts exhibited inhibition levels of from about 48% to about 77% at test levels from about 0.1 to about 3.8 mg/mL. At a test level from about 0.1 to about 0.2 mg/mL, the extracts exhibited an inhibition level of from about 59% to about 65%. The rice flour extracts exhibited activity after being stored for certain periods of time under various conditions. For example, RFE-25 exhibited an inhibition of about 63% at a test level of 1.0 mg/mL after being stored at 4° C. for about 20 days. After being stored at −20° C. for about 15 days, RFE-88 still exhibited an inhibition of about 59% at the 0.1 mg/mL level. As another example, RFE-100 exhibited an inhibition level of about 78% at a test level 1.1 mg/mL after being freeze-dried and stored for about 28 days.

Cultures of *H. influenzae* were treated with test samples and a control (HBSS+30 mM HEPES) using the same bacterial concentration and incubation time (15 minutes) as those used in the anti-adhesion assay. Following incubation, the bacteria/sample mixtures were plated on chocolate agar plates, incubated for 24 hours, and viable colonies were counted. The results showed no bactericidal activity of the two samples. This indicates that the anti-*H. influenzae* activity of the rice flour extract is inhibition of bacterial adhesion to the host cells.

Once it was determined that the crude extract of the rice flour was active, various tests were performed to characterize the active component of the rice flour extract.

In one test, after being separated from the insoluble residues, the crude extract was subjected to high pressure size exclusion chromatography (HPSEC). The mobile phase for the chromatographic analysis was the same type of solution as the extraction solution used to initially extract the crude extract. For example, if PBS were used in the initial extraction, then it would also be used as the mobile phase in the HPSEC. As another example, if ammonium bicarbonate were used in the initial extraction, then it would also be used as the mobile phase for the HPSEC.

The crude extract was subjected to a second HPSEC in which the mobile phase was water. After collecting an active fraction of the semi-purified extract, that active fraction was freeze dried. After freeze drying, the extract was then subjected to HPSEC using water as the mobile phase and was discovered to still demonstrate antibacterial activity.

EXAMPLE 2

HPSEC Fractionation of Crude Extract

An active PBS crude extract was first fractionated by high pressure size exclusion chromatography (HPSEC) using PBS as the mobile phase (PBS-HPSEC). The column used was a Varian MicroPak TSKgel-G3000 PWXL column measuring 7.8 mm in diameter (ID) and 30 cm in length (L) with a TSK PWXL guard column measuring 6.0 mm ID and 4.0 cm L. The flow rate used was 0.80 mL/minute. The sample was dissolved in water at 2.2 to 3.8 mg/mL and the injection volume was 200 μL per run. The detection was UV absorption at 214 nm and 2.0 AUFS (absorption unit full scale) and RI absorption at ×100 in series. Fractions were collected automatically at 1.25 minute intervals or 1.0 mL per fraction. A collection delay of 0.78 minute was determined and set to compensate for the travel time of the eluent from the UV detector to the fraction collector.

The active component was reproducibly eluted mainly in fraction 9 (retention time=10.00–11.25 min) and some in fraction 10 (retention time=11.25–12.50 min). Table 3 shows the activities of fractions surrounding the active fractions from several PBS-HPSEC runs using PBS crude extracts from two different sources of rice flour, one from ICN Biochemicals and one from Comet Rice Ingredients Company. In the table, "RFE" represents crude rice flour extract, the number indicates the run number of the extraction, "P" indicates PBS was used as the mobile phase for the HPSEC, and "ICN" and "Comet" indicate the commercial source of the rice flour used for the extraction.

TABLE 3

Anti-*H. influenzae* Activities of PBS-HPSEC Fractionations
% Inhibition by Fraction

| Starting Material* | F7 | F8 | F9 | F10 | F11 |
|---|---|---|---|---|---|
| RFE-101-1P (ICN) | −3 | 8 | 67 | 35 | −2 |
| RFE-101-2P (ICN) | 14 | −1 | 70 | 48 | 13 |
| RFE-1130-1P (ICN) | −20 | −12 | 74 | 21 | −15 |
| RFE-45P (ICN) | — | −5 | 59 | 14 | — |
| RFE-0510P (ICN) | −21 | −14 | 66 | 59 | 0 |
| RFE-0511P (ICN) | −27 | −15 | 69 | 55 | 1 |
| RFE-0512P (ICN) | −27 | −33 | 53 | −5 | −23 |
| RFE-0517P (ICN) | −14 | 4 | 63 | 42 | −18 |
| RFE-0422P (Comet) | −28 | −26 | 62 | 33 | −18 |

The active fraction 9 (F9) was collected, freeze dried, and fractionated again through the same HPSEC system but using water as the mobile phase (Water-HPSEC). In Water-HPSEC, the active component was eluted earlier and spread over three fractions 7, 8 and 9 (RT=7.50–11.25 min). Table 4 shows the activities fractions surrounding the active ones from several Water-HPSEC runs. Both the PBS-HPSEC and the Water-HPSEC fractionations were reproducible. Where, "W" after each run number indicates water was used as the mobile phase for the HPSEC, and "WF-7" of the last sample represents the Water-HPSEC fraction 7 of RFE-0525W (the fourth sample).

TABLE 4

Anti-*H. influenzae* Activities of Water-HPSEC Fractionations
% Inhibition by Fraction

| Starting Material* | F6 | F7 | F8 | F9 | F10 |
|---|---|---|---|---|---|
| RFE-0224W (ICN) | 18 | 69 | 68 | 49 | 11 |
| RFE-0510W (ICN) | 37 | 67 | 67 | 55 | 4 |
| RFE-0515W (ICN) | −3 | 44 | 44 | 38 | −15 |
| RFE-0525W (ICN) | 14 | 54 | 49 | 52 | 4 |
| RFE-0525W3 (ICN) | 27 | 67 | 67 | 67 | 38 |
| RFE-0606W (Comet) | 23 | 55 | 54 | 54 | 13 |
| WF-7-0605W (ICN) | −9 | 43 | −4 | −13 | −23 |

An active $NH_4HCO_3$ crude extract was also fractionated by the same HPSEC system using 0.2 N $NH_4HCO_3$ as the mobile phase ($NH_4HCO_3$-HPSEC). Table 5 shows the $NH_4HCO_3$-HPSEC profiles of the $NH_4HCO_3$ crude extract from Comet RF-M1080 rice flour, where "RF-M" indicates a medium grain rice flour. The active component was eluted mainly in fraction 9 and some in fraction 10, similar to the PBS crude extract in the PBS-HPSEC fractionation.

TABLE 5

$NH_4HCO_3$-HPSEC Fractionation and Bioactivity

| HPSEC Fraction | % Wt.* | % Inhibition | Bioactivity Test Level (mg/mL) |
|---|---|---|---|
| 5 | <0.2 | −12 | <0.6 |
| 6 | 15 ± 4 (3) | −3 | 0.13 |
| 7 | 18 ± 1 (4) | −4 | 0.19 |
| 8 | 6.2 ± 0.4 (4) | 1 | 0.06 |
| 9 | 8.9 ± 1.4 (4) | 58 | 0.13 |
| 10 | 20 ± 9 (4) | 48 | 0.38 |
| 11 | 9.8 ± 1.4 (4) | −5 | 0.13 |
| 12 | 12 ± 5 (4) | −5 | 0.06 |
| 13 | 3.8 ± 2.3 (3) | −5 | 0.06 |
| 14 | 0.8 | 6 | <0.06 |

Starting material was $NH_4HCO_3$ crude extract of Comet RF-M1080 rice flour.
*Values in parenthesis are number of preparations on separate days.

The extract was also subjected to a sequential organic solvent extraction. The crude extract was extracted with a first organic solvent mixture and then a second organic solvent mixture. The first organic solvent mixture comprises chloroform/methanol/water (1:1:0.2 v/v/v) and the second solvent mixture comprises isoproponol/hexane/water (11:5:3, v/v/v).

extract would have neutral lipid properties. If the extract was soluble in solvent C, then the extract would have polar lipid properties. Table 6 shows the percent distribution and bioactivity of each subfraction of the three active Water-HPSEC fractions.

All three Water-HPSEC active fractions did contain various amounts of extractables in the two organic solvent mixtures: 13–22% in solvent A and 11–23% in solvent C. The insolubles constituted 45–75%. Both the solvent C extract and the insoluble fraction of RFE-0606W-F8 were active (56% and 76% inhibition, respectively) at 0.5 mg/mL. Only the insoluble fraction of RFE-0606W-F9 was active (66% inhibition) at 0.25 mg/mL. The solvent C extract and the insoluble fraction of RFE-0606W-F7 were not tested. All solvent A extracts of the three Water-HPSEC fractions were not active at 0.25–0.5 mg/mL. Because the active extracts were soluble in solvent C and not solvent A, it was determined that this active extract was a polar lipid. Another component was in the insoluble fractions and was much more polar and hydrophilic than the active polar lipid.

Sequential organic solvent extraction was also used to fractionate the PBS and the $NH_4HCO_3$ crude extracts of a Comet RF-M1080 rice flour. A larger sample size was used for the extraction: 324 mg for the PBS crude extract and 46 mg for the $NH_4HCO_3$ crude extract. Table 6 shows the percent weight distribution and the corresponding bioactivity of each fraction. The active component of either the PBS crude extract or the $NH_4HCO_3$ crude extract was not extracted into either one of the two organic solvent mixtures. It remained in the insoluble portion. The difference from the above results of Water-HPSEC active fractions may be attributed to the much higher concentration of nonactive components in the crude extracts (>98.5% in PBS and >90% in $NH_4HCO_3$ crude extract).

TABLE 6

Sequential Organic Solvent Extraction And Bioactivity

| Sample | Solvent A* Extract | | Solvent C* Extract | | Residue | |
|---|---|---|---|---|---|---|
|  | % Wt | Activity** | % Wt | Activity** | % Wt | Activity** |
| RFE-0606W-F7 | 21.7% | −17% | 23.3% | — | 45.0% | — |
| RFE-0606W-F8 | 21.7% | −44% | 19.7% | 56% | 68.8% | 76% |
| RFE-0606W-F9 | 13.2% | −10% | 10.9% | 24% | 75.1% | 66% |
| PBS | 91.3% | −13% | 12.8% | −27% | 1.5% | −2% |
| RFE-0813/14*** | 23.2% | −8% | 2.8% | −11% | 62.5% | 67% |
| RFE-0422*** | 56.9% | −12% | 15.3% | −8% | 21.4% | 64% |

*Solvent A = chloroform/methanol/water (1:1.0.2, v/v/v)
Solvent C = isopropanol/hexane/water (11:5:3, v/v/v)
**% inhibition.
***RFE-0813/14 = $NH_4HCO_3$ crude extract of Comet RF-M1080, began with 46.1 mg.
RFE-0422 = PBS crude extract of Comet RF-M1080, began with 324.0 mg.

EXAMPLE 3

Sequential Organic Solvent Extraction

The above active Water-HPSEC fractions RFE-0606W-F7 to F9 (6 to 47 mg) of the PBS extract of Comet RF-M1080 rice flour were fractionated by sequential organic solvent extraction with 20 mL of an organic solvent mixture A first, followed by 20 mL of another organic solvent mixture C. Solvent A was chloroform/methanol/water (1:1:0.2, v/v/v) and solvent C was isopropanol/hexane/water (11:5:3, v/v/v). The purpose was to see if any water soluble lipid, such as glycolipid, would be present in these fractions which would be extracted by either or both organic solvent mixtures. If the extract was soluble in solvent A, then the The extract obtained from the water HPSEC was subjected to sequential ultrafiltration to determine the molecular size of the active component. The ultrafiltration apparatus included a pair of ultrafiltration membranes of nominal molecular weight cutoff (MWCO) at about 3,000 dalton and about 1,000 dalton, respectively.

EXAMPLE 4

Ultrafiltration of Active Fraction

A Water-HPSEC active fraction 8 (F8) from the PBS-HPSEC active fraction 9 of the PBS crude extract (RFE-0525W-F8, see Table 4) was filtered sequentially through two ultrafiltrabon membranes of nominal MWCO at about 3,000 dalton and about 1,000 dalton, respectively. The fraction that passed through both membranes demonstrated the best activity (71% inhibition) while the fraction which passed through the 3,000 dalton membrane and not the 1000 dalton membrane exhibited an inhibition of 14%. The portion which did not pass through either membrane exhibited minimal or no inhibition ability. This result, shown in Table 7, and the PBS-HPSEC result indicate that the active components are small molecules with molecular weights less than or equal to about 1,000 dalton.

TABLE 7

Ultrafiltration and Bioactivity

| Sample | Molecular Weight | % Inhibition | Test Level |
|---|---|---|---|
| RFE-0525W-F8 | ≥3000 D | 2 | 0.5 mg/mL EQ |
| RFE-0525W-F8 | 1000–3000 D | 14 | 0.5 mg/mL EQ |
| RFE-0525W-F8 | ≤1000 D | 71 | 0.5 mg/mL EQ |

The crude extract obtained from the original extraction was also subjected to a reverse phase chromatographic analysis. A C18-SPE (solid phase extraction) column was used to chromatograph the crude extract. Desirably, the mobile phase comprises a series of eluents. Those eluents are water, an ethanol-water mixture and ethanol. The extracts obtained from the various HPSEC can also be subjected to the sequential organic solvent extraction. The order of further separations and purification of the rice flour crude extract can be altered. For example, the crude extract from ammonium bicarbonate extraction of rice flour can be freeze dried, separated by sequential organic solvent extraction, and further purified by C18-SPE column and HPSEC or RP-HPLC.

EXAMPLE 5

Reverse Phase Chromatography

C18-SPE column chromatography was used to fractionate both the PBS and the $NH_4HCO_3$ crude extracts. Part of the active component of the $NH_4HCO_3$ crude extract was retained and part was not retained by a C18-SPE column (10 g) when 20 mL of the sample solution in water at 0.56 mg/mL was passed through the column. The active component of the PBS crude extract was not retained by the C18-SPE column (10 g) when 20 mL of the sample solution (5.83 mg/mL in water) was passed through the column. The retained active component of the $NH_4HCO_3$ crude extract was then eluted off with stronger solvents: water containing 10% and 50% ethanol. Table 8 shows the results.

TABLE 8

C18-SPE Column Fractionation and Bioactivity

| Sample | Fraction | Eluent | Weight % | % Inhibition |
|---|---|---|---|---|
| A | 1 | 40 mL water | 32.4 | 63 |
| A | 2 | 40 mL water | 3.6 | 6 |
| A | 3 | 50 mL EtOH/water (1.9 v/v) | 18.0 | 54 |
| A | 4 | 50 mL EtOH/water (5/5 v/v) | 9.0 | 55 |
| A | 5 | 50 mL EtOH | <0.9 | −4 |
| B | 1 | 40 mL water | 80.0 | 53 |
| B | 2 | 40 mL water | 0.4 | 18 |
| B | 3 | 50 mL EtOH/water (1/9 v/v) | 3.1 | 13 |
| B | 4 | 50 mL EtOH/water | 0.7 | 15 |

TABLE 8-continued

C18-SPE Column Fractionation and Bioactivity

| Sample | Fraction | Eluent | Weight % | % Inhibition |
|---|---|---|---|---|
| B | 5 | 50 mL EtOH (5/5 v/v) | <0.1 | 18 |

Sample A is $NH_4HCO_3$ crude extract of Comet RF-M1080 rice flour.
Sample B is PBS crude extract of Comet RF-M1080 rice flour.

Because the active component was eluted from the C18-SPE column with water as the eluent, it was determined that the active component was soluble in water. Further evidence of water solubility was determined because aqueous solutions were used to extract the active component of the rice flour. Also, the same aqueous solutions and water were used as the mobile phase for the HPSEC fractionations. This indicates that the active component is soluble in water. It was determined that the solubility of the active component in water is at least about 1 mg/mL (w/v).

EXAMPLE 6

Anti-*H. influenzae* Activity Dose Response and $IC_{50}$

Three Water-HPSEC active fractions (RFE-0224W-F7, F8 and F9) and a PBS crude extract (RFE-46) were tested for their activities at various concentrations. The results of those tests are shown in Table 9 which shows the corresponding $IC_{50}$'s. $IC_{50}$ is the concentration of the test substance at which the inhibition activity is 50%. The results show that the Water-HPSEC fraction 7 (RFE-0224W-F7) is the most active fraction on the weight basis with an $IC_{50}$ of about 0.014 mg/mL. Since this fraction may actually contain 22% inactive substance (see Table 6), the $IC_{50}$ of the active component of this fraction could be as low as about 0.011 mg/mL or lower.

TABLE 9

Anti-*H. influenzae* Activity Dose Response and $IC_{50}$

| Sample* | Test Level (mg/mL) | % Inhibition | $IC_{50}$ (mg/mL) |
|---|---|---|---|
| RFE-46 | 1 | 74% | 0.22 |
| | 0.5 | 64% | |
| | 0.25 | 54% | |
| | 0.13 | 35% | |
| | 0.06 | 16% | |
| RFE-0224W-F7 | 0.1 | 70% | 0.014 |
| | 0.052 | 62% | |
| | 0.026 | 62% | |
| | 0.013 | 49% | |
| | 0.007 | 37% | |
| RFE-0224W-F8 | 0.24 | 64% | 0.057 |
| | 0.12 | 63% | |
| | 0.06 | 51% | |
| | 0.03 | 40% | |
| | 0.015 | 24% | |
| RFE-0224W-F9 | 0.64 | 52% | 0.59 |
| | 0.32 | 38% | |
| | 0.16 | 28% | |
| | 0.08 | 17% | |
| | 0.04 | −4% | |

*RFE-46 was a PBS crude extract on ICN rice flour. RFE-0224W-F7, F8 and F9 were the Water-HPSEC fractions of a PBS-HPSEC active fraction 9, which was isolated from a PBS crude extract of ICN rice flour.

EXAMPLE 7

In Vivo Activity of Rice Flour Extract

A neonatal rat model was used to test the in vivo activity of rice flour extract against nontypeable *H. influenzae*. The results demonstrate that the nice flour extract can inhibit the attachment and thus the growth of nontypeable H. influenzae in the nasopharynx of neonatal rats. Table 10 shows test results of the rice flour extract against H. influenzae in a neonatal rat model from four trials.

TABLE 10

In vivo activity of Rice Flour Extract against H. influenzae

| Treatment* | Inoculum Dose Trial | H.I. Recovered CFU/pup** | $Log_{10}$(CFU/mL) |
|---|---|---|---|
| HI + HBSS (untreated) | 1 | 1.8 | 4.80 ± 0.20 |
| HI + RFE-0205 @ 1 mg/mL | 1 | 3.3 | 3.92 ± 0.24 |
| HI + HBSS (untreated) | 2 | 2.1 | 2.33 ± 0.55 |
| HI + RFE-0205 @ 2 mg/mL | 2 | 21 | 2.86 ± 0.72 |
| HBSS (uninfected) | 2 | 0 | 0.22 ± 0.22 |
| HI + HBSS (untreated) | 3 | 190 | 4.75 ± 0.11 |
| HI + RFE-0205 @ 1 mg/mL | 3 | 660 | 1.70 ± 0.47 |
| HI + RFE-0205 @ 0.5 mg/mL | 3 | 860 | 2.22 ± 0.50 |
| HI + RFE-0205 @ 0.25 mg/mL | 3 | 720 | 2.54 ± 0.49 |
| HI + RFE-0520-R @ 1 mg/mL | 3 | 420 | 0.76 ± 0.39 |
| HBSS (uninfected) | 3 | 0 | 2.53 ± 0.75 |
| HI + HBSS (untreated) | 4 | $1.7 \times 10^7$ | 4.90 ± 0.21 |
| HI + RFE-0205 @ 2 mg/mL | 4 | $1.7 \times 10^7$ | 3.94 ± 0.60 |
| HBSS (uninfected) | 4 | 0 | 0 |

*HI = nontypeable H. influenzae
HBSS = Hank's balanced saline solution
RFE-0205 = rice flour crude extract
RFE-0205-R = rice flour crude extract
R = water soluble residue from sequential organic solvent extractions.
**Individually determined for each inoculum, except trial 4 where the inoculum dose was based on the plate count of the overnight and twice washed bacterial suspension.

In the test, overnight cultures of nontypeable H. influenzae were prepared, washed twice and diluted with Hank's Balanced Saline Solution (HBSS) to obtain a bacterial suspension of less than 100,000 colony forming units (CFU) per mL. Sample solutions of a rice flour crude extract (RFE-0205) and a refined fraction (RFE-0520-R) were prepared by dissolving in HBSS at 2 and 4 mg/mL. Two one-to-two serial dilutions (1 and 0.5 mg/mL) from the 2 mg/mL RFE-0205 solution were also prepared. The sample solution was mixed with an equal volume (1 mL) of the diluted bacterial suspension and incubated for 1 hour at 37° C. A bacterial control was prepared by mixing and incubating 1 mL HBSS with an equal volume of the diluted bacterial suspension. A solvent blank control was prepared by incubating 2 mL HBSS under the same condition.

The experimental and control mixtures were used to inoculate 24-hour-old or younger rat pups at 10 µL each intranasally. Twenty-four hours after administration, samples of nasopharyngeal fluid were obtained by the slow instillation of 25 µL of HBSS into the left naris and the initial 10 µL discharge from the right naris was collected for plate count. This procedure ensured that the fluid had passed through the nasopharynx. The nasal wash was then spread "as is" or diluted and then spread onto chocolate agar plates. The plates were incubated at 37° C. overnight and counted for the number of CFU's (an indicator of the number of viable bacteria).

Table 10 shows the average inoculum dose in CFU and the average H. influenzae recovered in $log_{10}$(CFU/mL) per rat pup for each group, 10 rat pups per group. The results showed that the rice flour extract is not bactericidal. After the one hour incubation at 37° C., the plate counts of experimental mixtures (HI+RFE's) were always higher than those of bacterial control mixtures (HI+HBSS).

In trials 1 and 4, the treated groups (HI+RFE) showed 10 fold (one log) reduction in the recovered bacteria as compared to the untreated groups (HI+HBSS), even at a very high inoculum dose of $1.7 \times 10^7$ CFU/pup. In trial 2, the treated group did not show reduction in the recovered bacteria when compared with the untreated group. However, the treated group (21 CFU/pup) was exposed to 10 times higher inoculum than the untreated group (2.1 CFU/pup) and the result was therefore not conclusive.

In trial 3, the in vivo activity of the rice flour extract was clearly demonstrated. When the bacterial suspension was preincubated with RFE-0205 at 1 mg/mL, a reduction of three logs (one thousand fold) in the number of bacteria recovered was observed in the treated group (1.70±0.47 $log_{10}$ CFU/mL) as compared to the untreated group (4.75±0.11 $log_{10}$ CFU/mL). A trend of dose response was also observed. The recovered bacteria progressively increased, although not statistically significant, from 1.70 to 2.54 $log_{10}$ CFU/mL as the RFE-0205 concentration decreased from 1 to 0.25 mg/mL.

A refined fraction RFE-0520-R from a crude extract prepared from a large scale production (10kg of rice flour extracted with 100 liters of 0.2N ammonium bicarbonate solution) also showed a very good anti-H. influenzae activity. At 1 mg/mL, the recovered H. influenzae of the group was 0.76±0.39 $log_{10}$ CFU/mL which is a ten thousand fold (4 logs) reduction in the number of bacteria recovered 24 hours post-inoculabon as compared to the untreated group.

The above results clearly demonstrate the in vivo activity of rice flour extract in inhibiting the attachment of nontypeable H. influenzae to nasopharynx of neonatal rats. This resulted in the prevention of the bacteria replication in the animal. It is interesting to compare the treated groups with the untreated group in trial 3, wherein the rice flour extract treated H. influenzae at much higher inoculum doses still resulted in 100–10,000 fold (2–4 logs) reduction in the number of recovered H. influenzae.

The rice flour extracts of the present invention can be used to formulate pharmaceutical compositions and nutritional compositions which can be administered to patients for the prophylaxis and treatment of infections caused by Haemophilus influenzae. An effective dose can be readily determined by the use of conventional techniques and by observing results obtained under analogous circumstances. In determining the effective dose, a number of factors are considered including, but not limited to, the following: the species of the patient; its size, age and general health; the specific illness involved; the degree of or involvement or the severity of the illness; the response of the individual patient; the mode of administration; the bioavailability characteristics of the preparation administered; the dose regimen selected; and the use of concomitant medication. Typically, these compositions are formulated to deliver either a dose of (1) from about 2 milligrams to about 24 milligrams of the active component of the rice flour extract; (2) from about 0.02 gram to about 1 gram of the rice flour extract; or (3) from about 0.1 gram to about 6 grams of the rice flour per 8 fluid ounces of liquid. Higher dosages can be used. Dosage rates are from about 3 to about 6 times per day, although fewer or more doses may be administered as necessary.

The pharmaceutical compositions of the present invention comprise an effective amount of the rice flour extract or its derivatives and pharmaceutically acceptable carriers and excipients. In one embodiment, the rice flour extract can be mixed with a carrier and formed into a tablet. The tablet may optionally be coated with a polymeric material which changes the dissolution rate of the tablet to sustain the release of the active component in the oral mucosa. In another embodiment, the extract can be mixed with a carrier and formed into multi-unit dosage granules. These granules can then be coated with a polymeric material which changes the dissolution rate of the granules to sustain the release of the active component in the oral mucosa. Useful carriers include, but are not limited to, lactose, sorbitol, starch, and gelatin. In still another embodiment, the rice flour extract can be formulated into a liquid preparation. In still another embodiment, the extract or its derivatives can be formulated into a nasal spray. The pharmaceutical formulations of this invention can also be formulated to include at least one nutrient selected from the group consisting of vitamins, minerals, carbohydrates, sugars, amino acids, free fatty acids, phospholipids, antioxidants, and phenolic compounds. The method of manufacture and useful materials for these embodiments are within the skill of a person skilled in the art and will not be discussed here.

The nutritional formulation can also be used for the prophylaxis and treatment of infections caused by *Haemophilus influenzae*. The nutritional formulation can be in solid or liquid form. As used herein, the term "nutritional formulation" refers to any type of formulation, whether solid or liquid, which can be used to provide additional nutrition to a patient and which includes those types of formulations which are known as dietary and mineral supplements. The nutritional formulation can be formulated to include at least one nutrient selected from the group consisting of vitamins, minerals, carbohydrates, sugars, amino acids, free fatty acids, phospholipids, antioxidants, and phenolic compounds. The nutritional formulation can also be formulated to include a flavoring and/or sweetening agent. Liquid preparations may include, beside the active ingredient, preservatives, dyes and colorings in addition to flavoring and sweetening agents.

Material used to formulate the pharmaceutical compositions and the nutritional compositions should be pharmaceutically pure or food-grade and non-toxic in the amounts used.

The present invention is also directed to a method for the prophylaxis and treatment of *Haemophilus influenzae* infections comprising administering to a patient an effective amount of a rice flour extract or its derivatives. The rice flour extract or its derivatives can be delivered in combination with at least one nutrient selected from the group consisting of vitamins, minerals, carbohydrates, sugars, amino acids, free fatty acids, phospholipids, antioxidants, and phenolic compounds. Useful dosages are described above.

The present invention is further directed to a method for the prophylaxis and treatment of otitis media comprising administering to a patient an effective amount of a rice flour extract or its derivatives. The rice flour extract or its derivatives can be delivered in combination with at least one nutrient selected from the group consisting of vitamins, minerals, carbohydrates, sugars, amino acids, free fatty acids, phospholipids, antioxidants, and phenolic compounds. Useful dosages are described above.

As used herein, the term "patient" refers to warm-blooded animals or mammals, including, but not limited to, mice, rats and humans. A patient is in need of treatment for a *Haemophilus influenzae* infection when the patient is suffering from symptoms, such as, for example, fever, otalgia, and hearing loss. A patient is in need of treatment for otitis media when the patient is suffering from symptoms, such as, for example, fever, otalgia, or hearing loss.

The identification of patients who are in need of treatment for a *Haemophilus influenzae* infection or otitis media is well within the ability and knowledge of a skilled practitioner. A practitioner skilled in the art can readily identify, by the use of clinical tests, physical examination and medical/family history, those patients in need of treatment for a *Haemophilus influenzae* infection or otitis is media. Successful treatment is also understood to include prophylaxis in treating a patient in those instances in which the patient has experienced a prior *Haemophilus influenzae* infection or otitis media occurrence and also in those instances when a patient has been deemed by a skilled practitioner to be a likely candidate for either a *Haemophilus influenzae* infection or otitis media.

INDUSTRIAL APPLICABILITY

Commercial food grade rice flours and non-food grade rice flours are relatively inexpensive commodities. A relatively inexpensive and effective product can be economically produced in large quantities.

The embodiments of the present invention may, of course, be carried out in other specific ways than those set forth herein without departing from the spirit and scope of the invention. The present embodiments are, therefore, to be considered in all respects as illustrative and not restrictive and that all changes and equivalents also come within the description of the present invention.

We claim:

1. A rice flour extract characterized by being soluble in water, having a molecular weight of less than or equal to about 1000 dalton, having an $IC_{50}$ of about 0.01 mg/mL to about 0.6 mg/mL for inhibiting the adhesion of *Haemophilus influenzae* to nasopharyngeal cells, and being insoluble in a solvent mixture consisting essentially of chloroform, methanol and water at a ratio of 1:1:0.2 by volume.

2. The rice flour extract of claim 1 wherein said rice flour extract is further characterized by being soluble in water at a level of at least 1 mg/mL.

3. The rice flour extract of claim 2 wherein said rice flour extract is further characterized by being soluble in a solvent mixture consisting essentially of isopropanol, hexane and water at a ratio of 11:5:3 by volume.

4. The rice flour extract of claim 3, wherein said rice flour extract is further characterized by having a retention time between from about 10.0 minutes to about 12.5 minutes in a high pressure size exclusion chromatographic analysis employing a Varian MicroPak TSKgel-G3000 PWXL column (7.8 mm ID×30 cm L) with a TSK PWXL guard column (6.0 mm ID×4.0 cm L) and using phosphate buffered saline solution as the mobile phase at a flow rate of 0.80 mL/minute.

5. A nutritional formulation formed from the rice flour extract of claim 1.

6. The nutritional formulation of claim 5 further including at least one nutrient selected from the group consisting of vitamins, minerals, carbohydrates, sugars, amino acids, free fatty acids, phospholipids, antioxidants and phenolic compounds.

7. A pharmaceutical composition formed from the rice flour extract of claim 1.

8. The pharmaceutical composition of claim 7 wherein said rice flour extract is mixed with a carrier and is formed into a tablet.

9. The pharmaceutical composition of claim 8 wherein said tablet is coated with a polymeric material which changes the dissolution rate of the tablet to sustain the release of the active component in the oral mucosa.

10. The pharmaceutical composition of claim 7 wherein said rice flour extract is mixed with a carrier and formed into multi-unit dosage granules.

11. The pharmaceutical composition of claim 10 wherein said granules are coated with a polymeric material which changes the dissolution rate of the granules to sustain the release of the active component in the oral mucosa.

12. The pharmaceutical composition of claim 7 wherein said rice flour extract is formulated into a liquid preparation.

13. The pharmaceutical composition of claim 7 further including at least one nutrient selected from the group consisting of vitamins, minerals, carbohydrates, sugars, amino acids, free fatty acids, phospholipids, antioxidants and phenolic compounds.

14. A method for the prophylaxis and treatment of *Haemophilus influenzae* infections comprising administering to a patient an effective amount of a rice flour extract or its derivatives, wherein said rice flour extract is characterized by being soluble in water, having a molecular weight of less than or equal to about 1000 dalton, having an $IC_{50}$ of about 0.01 mg/mL to about 0.6 mg/mL for inhibiting the adhesion of *Haemophilus influenzae* to nasopharyngeal cells, and being insoluble in a solvent mixture consisting essentially of chloroform, methanol and water at a ratio of 1:1:0.2 by volume.

15. The method of claim 14 wherein said rice flour extract is soluble in water at a level of at least 1 mg/mL.

16. The method of claim 15 wherein said rice flour extract is further characterized by being soluble in a solvent mixture consisting essentially of isopropanol, hexane and water at a ratio of 11:5:3 by volume.

17. The method of claim 16 wherein said rice flour extract is further characterized by having) a retention time between from about 10.0 minutes to about 12.5 minutes in a high pressure size exclusion chromatographic analysis employing a Varian MicroPak TSKgel-G3000 PWXL column (7.8 mm ID×30 cm L) with a TSK PWXL guard column (6.0 mm ID×4.0 cm L) and using phosphate buffered saline solution as the mobile phase at a flow rate of 0.80 mL/minute.

18. The method of claim 14 wherein said rice flour extract or its derivatives is delivered in combination with at least one nutrient selected from the group consisting of vitamins, minerals, carbohydrates, sugars, amino acids, free fatty acids, phospholipids, antioxidants and phenolic compounds.

19. A method for the prophylaxis and treatment of otitis media comprising administering to a patient an effective amount of a rice flour extract or its derivatives, wherein said rice flour extract is characterized by being soluble in water, having a molecular weight of less than or equal to about 1000 dalton, having an $IC_{50}$ of about 0.01 mg/mL to about 0.6 mg/mL for inhibiting the adhesion of *Haemophilus influenzae* to nasopharyngeal cells, and being insoluble in a solvent mixture consisting essentially of chloroform, methanol and water at a ratio of 1:1:0.2 by volume.

20. The method of claim 19 wherein said rice flour extract is further characterized by being soluble in water at a level of at least about 1 mg/mL.

21. The method of claim 20 wherein said rice flour extract is further characterized by being soluble in a solvent mixture consisting essentially of isopropanol, hexane and water at a ratio of 11:5:3 by volume.

22. The method of claim 21 wherein said rice flour extract is further characterized by having a retention time between from about 10.0 minutes to about 12.5 minutes in a high pressure size exclusion chromatographic analysis employing a Varian MicroPak TSKgel-G3000 PWXL column (7.8 mm ID×30 cm L) with a TSK PWXL guard column (6.0 mm ID×4.0 cm L) and using phosphate buffered saline solution as the mobile phase at a flow rate of 0.80 mL/minute.

* * * * *